(12) United States Patent
Tanaka et al.

(10) Patent No.: US 9,975,657 B2
(45) Date of Patent: May 22, 2018

(54) STERILIZATION DEVICE FOR CONTAINER

(71) Applicant: MITSUBISHI HEAVY INDUSTRIES FOOD & PACKAGING MACHINERY CO., LTD., Nagoya-shi, Aichi (JP)

(72) Inventors: Daisuke Tanaka, Tokyo (JP); Shigehiro Sugiyama, Tokyo (JP); Yasue Takeuchi, Tokyo (JP); Sugihiko Yui, Nagoya (JP)

(73) Assignee: MITSUBISHI HEAVY INDUSTRIES MACHINERY SYSTEMS, LTD., Kobe-shi, Hyogo (JP)

( * ) Notice: Subject to any disclaimer, the term of this patent is extended or adjusted under 35 U.S.C. 154(b) by 80 days.

(21) Appl. No.: 14/771,051

(22) PCT Filed: Mar. 12, 2014

(86) PCT No.: PCT/JP2014/001394
§ 371 (c)(1),
(2) Date: Aug. 27, 2015

(87) PCT Pub. No.: WO2014/148007
PCT Pub. Date: Sep. 25, 2014

(65) Prior Publication Data
US 2016/0009433 A1    Jan. 14, 2016

(30) Foreign Application Priority Data
Mar. 18, 2013    (JP) .................................. 2013-054506

(51) Int. Cl.
*B65B 55/10*    (2006.01)
*A61L 2/00*    (2006.01)
(Continued)

(52) U.S. Cl.
CPC ................. *B65B 55/10* (2013.01); *A61L 2/00* (2013.01); *A61L 2/20* (2013.01); *A61L 2/208* (2013.01); *A61L 9/00* (2013.01)

(58) Field of Classification Search
CPC .................................. A61L 2/20; B65B 55/10
See application file for complete search history.

(56) References Cited

U.S. PATENT DOCUMENTS 1,998,764 A * 4/1935 Jordan ..................... H05B 3/70
                                                              219/467.1
4,537,749 A    8/1985 Hick
(Continued)

FOREIGN PATENT DOCUMENTS

CN      1447701 A    10/2003
CN    101018711 A     8/2007
(Continued)

OTHER PUBLICATIONS

English Machine Translation of JP 05-23454. Mitsubishi Heavy Ind. Ltd. Jun. 16, 1993.*
(Continued)

*Primary Examiner* — Donald R Spamer
(74) *Attorney, Agent, or Firm* — Manabu Kanesaka; Benjamin Hauptman; Kenneth Berner

(57) ABSTRACT

Provided is a sterilization device for a container which exhibits high sterilization performance while being low in cost. A heating medium is positioned in a sterilant passage so as to block the downstream end thereof in the direction in which the liquid sterilant is discharged. A ventilation passage is formed in the lateral surface of a tube body of a sterilant supply tube, on the upstream side in the direction in which the liquid sterilant is discharged in relation to the heating medium. A sterilant supply unit sterilizes the inner-peripheral surface of a container as a result of the sterilant vaporizing upon reaching the heating medium, leaking to the
(Continued)

exterior via the ventilation passage formed in the lateral surface of the tube body, and adhering to the inner-peripheral surface of the container.

10 Claims, 8 Drawing Sheets

(51) Int. Cl.
*A61L 9/00* (2006.01)
*A61L 2/20* (2006.01)

(56) References Cited

U.S. PATENT DOCUMENTS

| | | | |
|---|---|---|---|
| 4,896,478 A | 1/1990 | Reiter | |
| 6,702,985 B1 * | 3/2004 | Taggart | B67C 7/0073 222/356 |
| 6,786,249 B2 | 9/2004 | Armbruster et al. | |
| 6,899,856 B2 | 5/2005 | Itoh et al. | |
| 6,984,360 B1 | 1/2006 | Feuilloley et al. | |
| 7,685,794 B2 | 3/2010 | Nagatani et al. | |
| 8,388,761 B2 | 3/2013 | Iwashita et al. | |
| 2008/0107562 A1 | 5/2008 | Hayashi et al. | |
| 2009/0129975 A1 | 5/2009 | Colato et al. | |
| 2014/0144105 A1 | 5/2014 | Hayakawa et al. | |

FOREIGN PATENT DOCUMENTS

| | | |
|---|---|---|
| CN | 101460261 A | 6/2009 |
| DE | 102006036462 A1 | 2/2008 |
| EP | 1142592 A1 | 10/2001 |
| GB | 2 089 213 A | 6/1982 |
| JP | H03-224469 A | 10/1991 |
| JP | H03-226444 A | 10/1991 |
| JP | H05-23454 Y2 | 6/1993 |
| JP | H11-227725 A | 8/1999 |
| JP | 2007-020744 A | 2/2007 |
| JP | 4493592 B2 | 6/2010 |
| WO | 2012/003903 A1 | 1/2012 |

OTHER PUBLICATIONS

China Patent Office, "Office Action for Chinese Patent Application No. 201480008347.9," dated Apr. 1, 2016.
China Patent Office, "Office Action for Chinese Patent Application No. 201480008347.9," dated Nov. 2, 2016.
Europe Patent Office, "Search Report for European Patent Application No. 147700779.3," dated Sep. 16, 2016.
PCT, "International Search Report for International Application No. PCT/JP2014/001394".

* cited by examiner

FIG. 4A
FIG. 4B
FIG. 4C
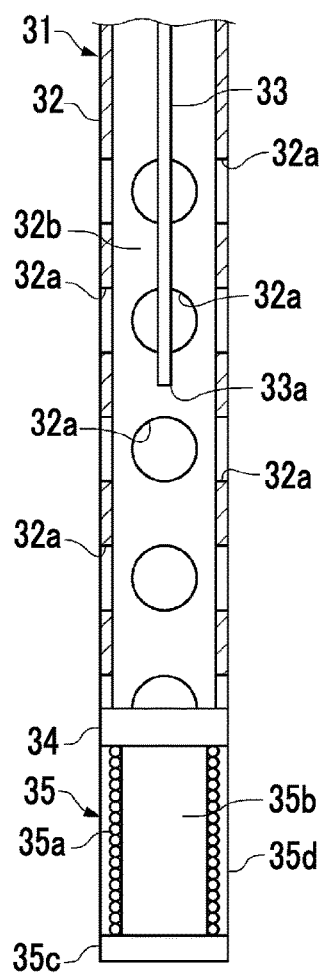
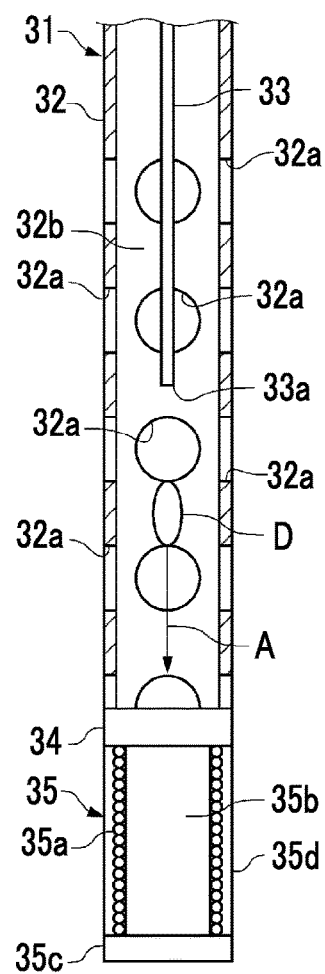
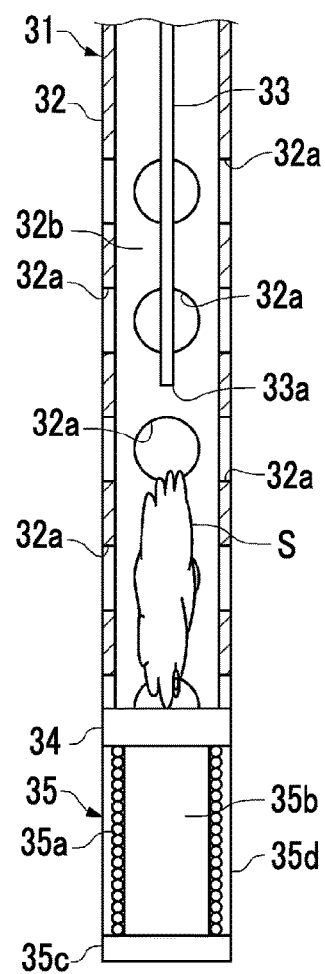

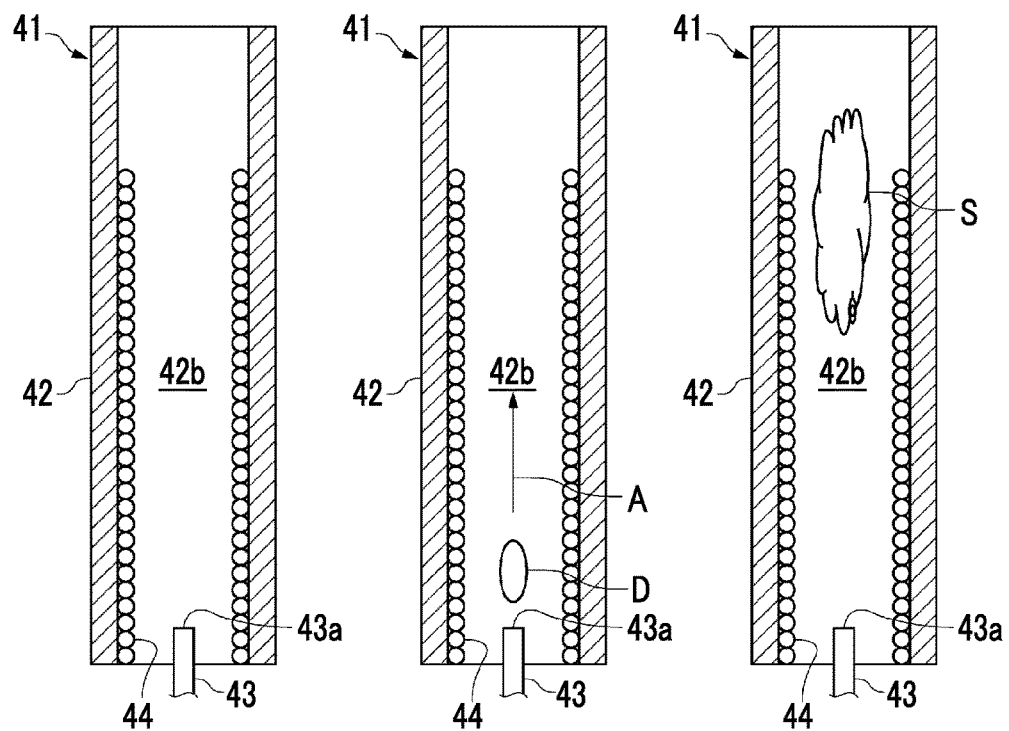

STERILIZATION DEVICE FOR CONTAINER

RELATED APPLICATIONS

The present application is National Phase of International Application No. PCT/JP2014/001394 Mar. 12, 2014, and claims priority from Japanese Application No. 2013-054506, filed Mar. 18, 2013, the disclosure of which is hereby incorporated by reference herein in its entirety.

TECHNICAL FIELD

The present invention relates to a device which supplies a sterilant into a container for beverages, and typically a PET bottle for sterilization.

BACKGROUND ART

In a case of aseptic filling of tea, fruit juice beverages, coffee beverages, and the like, the inside and the outside of a container to be filled with such a beverage needs to be sterilized before the container is filled with the beverage. Therefore, in a method of sterilizing a molded container such as a paper container or a plastic container such as a PET bottle, an aqueous solution of peracetic acid (with a rational formula of $CH_3C(=O)OOH$) or an aqueous solution of hydrogen peroxide ($H_2O_2$) is mainly used. In addition, in a case where a container as a sterilization object has a deep bottom shape or an uneven shape, a method of sterilizing the container by spraying a sterilant toward the sterilization object and drying the container is known. In addition, a method of sterilizing a container by heating a sterilant to its boiling point or higher so as to be vaporized, spraying the vaporized sterilant into the air to be condensed which adheres to the container as fine mist, and drying the container is also known.

However, in the sterilization methods according to the related art, a high concentration of hydrogen peroxide is used, and thus the sterilizing ability is sufficient. However, the hydrogen peroxide adsorbs onto and penetrates into the surface layer of the container, and it takes time for the removal of the hydrogen peroxide. Therefore, the sterilization process cannot be shortened. Here, Patent Document 1 proposes, as a method of reliably performing sterilization at a high speed, a method of introducing a mist of hydrogen peroxide condensed and generated after temporarily vaporizing droplets of hydrogen peroxide into a pre-heated PET bottle and blowing hot air into the PET bottle.

CITATION LIST

Patent Literature

[Patent Document 1] Japanese Patent No. 4493592

SUMMARY OF INVENTION

Technical Problem

In the sterilization method in Patent Document 1, the droplets of hydrogen peroxide are generated by mixing an aqueous solution of hydrogen peroxide with compressed air in a two-fluid spray. Therefore, although the sterilization method of Patent Document 1 has high sterilization performance, the two-fluid spray and the compressed air are needed in order to generate the mist of hydrogen peroxide. Therefore, sterilant cost is increased and the concentration of hydrogen peroxide is reduced due to the dilution with the air.

The invention has been made on the basis of the problems, and an object thereof is to provide a sterilization device for a container, which has high sterilization performance with low cost.

Solution to Problem

A sterilization device of the invention includes a sterilant supply tube which has a sterilant passage inside the sterilant supply tube, through which a discharged sterilant in liquid form passes in a state in which the sterilant supply tube is inserted into a container as a sterilization object, a heating medium which heats and vaporizes the sterilant that passes through the sterilant passage, and a ventilation passage which allows the sterilant heated and vaporized by the heating medium to leak out of the sterilant supply tube.

The sterilization device of the invention heats and vaporizes the sterilant inside the container and allows the vapor to adhere to the inner surface of the container as it is, and thus can realize high sterilization performance with low cost.

The sterilization device of the invention includes at least a first embodiment and a second embodiment.

In the sterilization device according to the first embodiment, the heating medium is disposed to block a downstream side in a direction in which the sterilant in the liquid form is discharged in the sterilant passage, the ventilation passage is formed in a side surface of the sterilant supply tube and is formed closer to an upstream side in the direction in which the sterilant in the liquid form is discharged than the heating medium. In the sterilization device according to the first embodiment, the sterilant that reaches the heating medium and vaporizes leaks out through the ventilation passage, to the outside that is, to the inside of the container, formed in the side surface of the sterilant supply tube. The sterilant which leaks out to the inside of the container, adheres to the inside of the container to perform sterilization.

In the first embodiment, it is preferable that a plurality of ventilation passages are provided in the side surface of the sterilant supply tube in order to allow the vaporized sterilant to be reliably adhered to the inner surface of the container.

In the sterilization device according to the first embodiment, in a case where a heat source which heats the heating medium is provided, it is preferable that a heat source is disposed on an opposite side of the sterilant supply tube with respect to the heating medium in an axial direction of the sterilant supply tube and has dimensions in a radial direction of the heat source that are equal to or smaller than those in a radial direction of the sterilant supply tube. When the sterilant supply tube is inserted into or removed from the container, obstacle can be prevented.

In the sterilization device according to the second embodiment, the heating medium is disposed to have a predetermined length along the sterilant passage, the ventilation passage is formed at a downstream end in a direction in which the sterilant in the liquid form is discharged in the sterilant supply tube, In the sterilization device according to the second embodiment, the sterilant that is vaporized in a process of moving along the heating medium leaks out through the ventilation passage formed at the downstream end of the sterilant supply tube.

In the sterilization device according to the second embodiment, the heating medium may be configured to surround the sterilant passage.

In this case, since the sterilant that passes through the sterilant passage is heated from all around the periphery thereof, thus the sterilant can be efficiently vaporized.

Advantageous Effects of Invention

The sterilization device of the invention heats and vaporizes the sterilant inside the container and allows the vapor to adhere to the inner surface of the container as it is, and thus can realize high sterilization performance with low cost.

BRIEF DESCRIPTION OF DRAWINGS

FIGS. 4(a) to 4(c) are partially enlarged longitudinal sectional views of the sterilant supply tube illustrated in FIGS. 1 and 2.

FIGS. 8(a) to 8(c) are enlarged longitudinal sectional views of a sterilant supply tube in the second embodiment of the invention.

DESCRIPTION OF EMBODIMENTS

First Embodiment

Hereinafter, a sterilization device for a container of the invention will be described on the basis of an embodiment applied to an aseptic beverage filling machine.

Figure 1:
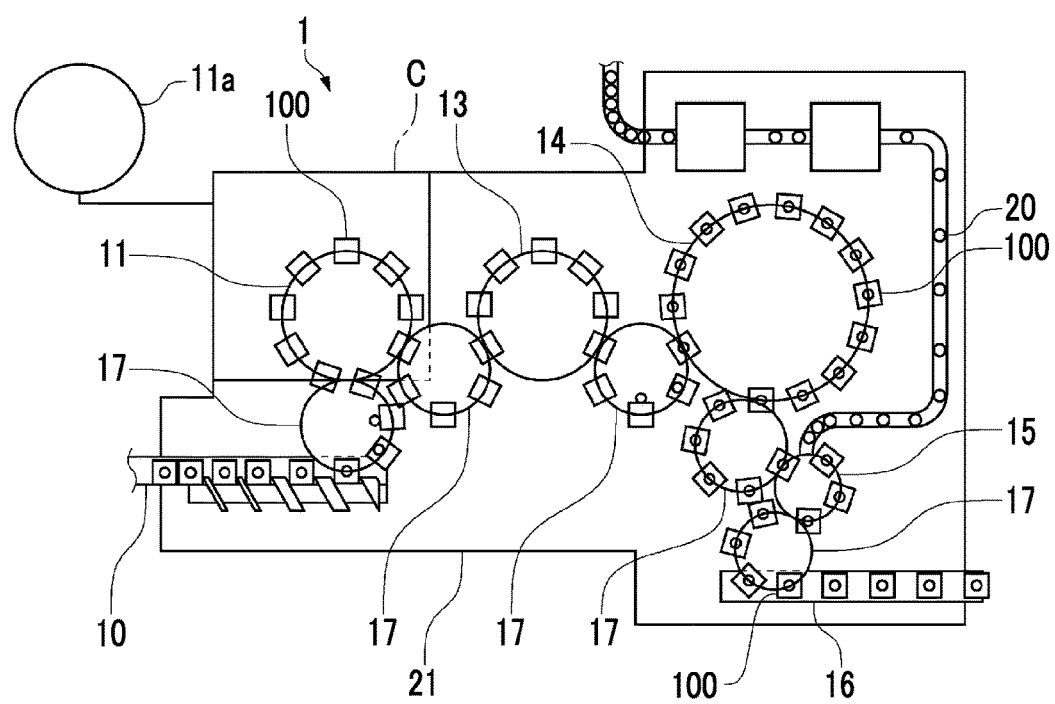
FIG. 1 is a view illustrating a schematic configuration of an aseptic beverage filling machine in a first embodiment of the invention.

As illustrated in FIG. 1, an aseptic beverage filling machine 1 includes, as constituent elements, an importing conveyor 10 which imports a container 100 to the aseptic beverage filling machine 1, a sterilization device 11 which sterilizes the container 100, a rinsing device 13 which rinses the container 100, a filling device 14 which fills the container 100, which is subjected to sterilization and rinsing, with a liquid (beverage), a capper 15 which attaches a cap 20 to the container 100 filled with the beverage, and an exporting conveyor 16 which exports the container 100 to the outside of the aseptic beverage filling machine 1. Transporting star wheels 17 are provided between the constituent elements so that the container 100 can be transported between the constituent elements.

The transport path of the container 100 in the sterilization device 11, the rinsing device 13, the filling device 14, and the capper 15 is provided on a base support 21. On the base support 21, a chamber C which covers the sides and the upper side of a space on the base support 21 is provided to maintain the transport path of the container 100 in the sterilization device 11, the rinsing device 13, the filling device 14, and the capper 15 in a sterile environment.

In addition, in the chamber C, a shower-like or sprinkler-like spray nozzle (not illustrated) is provided to spray a sterilant, a rinsing liquid, and the like into the chamber C.

In addition, a drain port (not illustrated) is formed in the base support 21 to recover the sprayed sterilant or the rinsing liquid, and the revered sterilant and the like are discharged to an external recovery unit through the drain port.

A sterilant supply unit 11a is provided in association with the sterilization device 11. The sterilant supply unit 11a supplies the sterilant to the chamber C and the sterilization device 11. The sterilant supplied to the chamber C is used to sterilize the inside of the chamber C, and the sterilant supplied to the sterilization device 11 is used to sterilize the inside and the outside of the container 100. This embodiment is characterized in that the inside of the container 100 is sterilized as described below. In addition, as the sterilant, for example, chemicals such as peracetic acid and hydrogen peroxide may be applied.

Hereinafter, the details of the sterilization device 11 in the aseptic beverage filling machine 1 will be described with reference to FIGS. 2 to FIGS. 4(c).

The sterilization device 11 includes a sterilant supply unit 30 and a container holding unit 50. The sterilization device 11 sterilizes the inner surface of the container 100 during a process of transporting the container 100 while holding the container 100 with the container holding unit 50 of the transporting star wheels 17. However, the sterilization device 11 may also sterilize the container 100 in a state where the container 100 is stopped.

Hereinafter, the configuration of the sterilization device 11 will be described in order of the sterilant supply unit 30 and the container holding unit 50.

The sterilant supply unit 30 includes a sterilant supply tube 31, an elevating bar 36 which elevates the sterilant supply tube 31 while holding the sterilant supply tube 31, and a guide rail 39 which supports the elevating bar 36 so as to be elevated.

The guide rail 39 is provided on the base support 21 along the path on which the container 100 is transported.

Figure 2:
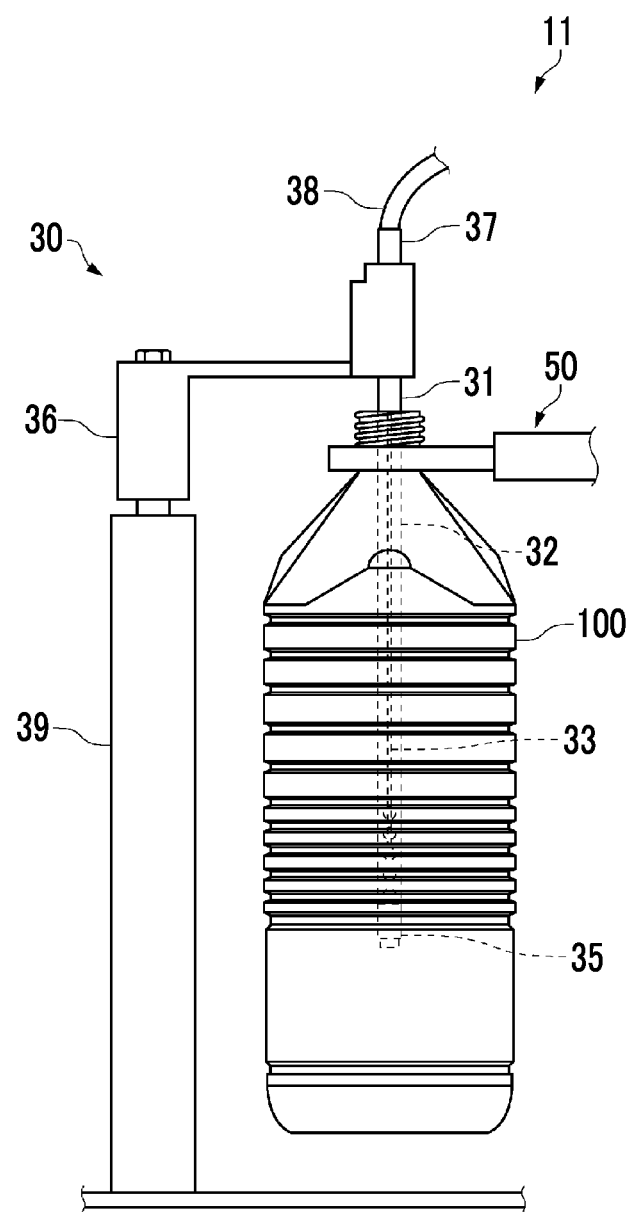
FIG. 2 is a view illustrating a sterilization device for a container applied to the aseptic beverage filling machine of FIG. 1.
Figure 3:
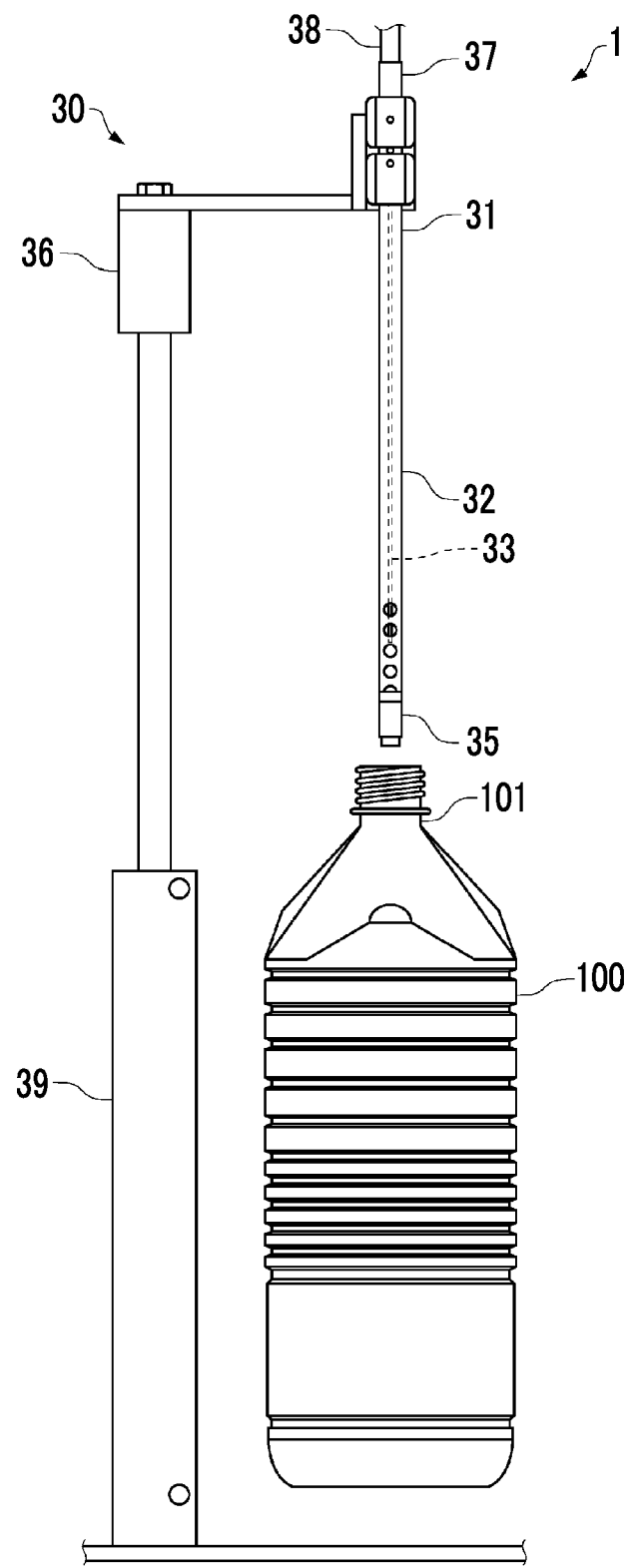
FIG. 3 is a view illustrating a state before a sterilant supply tube of the sterilization device illustrated in FIG. 2 is inserted into a container.

The elevating bar 36 can be elevated between an operation position illustrated in FIG. 2 and a standby position illustrated in FIG. 3, and is located at the standby position until a sterilization process is performed. When the container 100 is transported to a predetermined sterilization position, the sterilant supply tube 31 is lowered by a driving source (not illustrated) so that the sterilant supply tube 31 is inserted into the container 100 from the opening formed at the upper end of the container 100.

When the sterilant supply tube 31 is inserted into the container 100, the sterilant supply unit 30 supplies the sterilant in liquid form to the sterilant supply tube 31 and vaporizes the sterilant in the sterilant supply tube 31. The sterilant supply unit 30 allows the vaporized sterilant to leak toward the outside of the sterilant supply tube 31 and adhere to the inner surface of the container 100 for sterilization. This is the primary function of the sterilant supply unit 30, and in order to exhibit this function, the sterilant supply tube 31 includes the following configuration.

As illustrated in FIGS. 4(a) to 4(c), the sterilant supply tube 31 includes a hollow cylindrical tube body 32, a needle 33 which is disposed inside the tube body 32 to discharge the sterilant toward a heating medium, a heating medium 34 which seals the tip of the tube body 32, a heat source 35 which heats the heating medium 34, and a nozzle 37 (FIGS. 2 and 3) which supplies the sterilant to the needle 33. In addition, a side on which the sterilant supply tube 31 is inserted into the container 100 is defined as the tip, and a side on which the nozzle 37 is provided is defined as a rear end.

The tube body 32 is made of a metal material, and is preferably made of stainless steel due to the excellent corrosion resistance thereof. However, a material other than the metal material, for example, a ceramic material may also be used.

As illustrated in FIGS. 4(a) to 4(c), the tube body 32 includes ventilation passages 32a which penetrate through the tip side in the thickness direction and allow the vaporized sterilant to pass therethrough and leak toward the outside of the tube body 32. In this embodiment, a plurality of ventilation passages 32a having the same diameter are provided at equal intervals in the axial direction and are provided at equal intervals also in the peripheral direction. In addition, the ventilation passages 32a are formed closer to the upstream side in a direction in which the sterilant is discharged than the heating medium 34.

The needle 33 is a hollow cylindrical member and is, similar to the tube body 32, made of a metal material having excellent corrosion resistance.

The needle 33 includes a discharge port 33a which is open at the tip, and the rear end there of is connected to the nozzle 37. When the sterilant in the liquid form is supplied from the nozzle 37, the sterilant in droplet form is discharged from the discharge port 33a toward the heating medium 34. As illustrated in FIGS. 2 and 3, a tube 38 is connected to the nozzle 37, and the tube 38 is connected to the sterilant supply unit 11a and supplies the sterilant to the nozzle 37 via, for example, a syringe pump (not illustrated).

The discharge port 33a of the needle 33 is disposed at a predetermined interval from the heating medium 34, and the sterilant in droplet form discharged from the discharge port 33a falls in the tube body 32 and reaches the surface of the heating medium 34. This interval is arbitrary, and in consideration of the container 100 being sterilized while moving on the path along the transporting star wheels 17, has to be a distance such that the sterilant reaches the heating medium 34 due to centrifugal force.

The discharge port 33a of the needle 33 is positioned closer to the lower side than the rearmost ventilation passage 32a among the ventilation passages 32a provided in the axial direction.

The heating medium 34 heats and vaporizes the falling sterilant.

The heating medium 34 is a disk-shaped member having the same diameter as the outer diameter of the tube body 32 so as to seal the tip of the tube body 32 corresponding to the downstream end in the direction in which the sterilant is discharged, and similar to the tube body 32, is made of a metal material having excellent corrosion resistance. The heating medium 34 is joined to the tip of the tube body 32 by appropriate means such as welding, an adhesive, or the like.

The heat source 35 heats the heating medium 34.

The heat source 35 includes a heater 35a formed of electric heating wires wound in a spiral ring form, a core 35b on which the heater 35a is wound around the outer periphery of the core 35b, a holder 35c which supports the heater 35a in the axial direction, and a tube-shaped insulation sheath 35d which covers the heater 35a.

The heater 35a generates heat by being supplied with power from a power source (not illustrated), and directly heats the heating medium 34 and indirectly heats the heating medium 34 via the core 35b. For the electric heating wires used in the heater 35a, a well-known alloy primarily containing nickel and chromium, or an alloy primarily containing iron, chromium, and aluminum may be used.

The core 35b may be formed integrally with the heating medium 34, or may also be produced as a separate member so as to be joined to the tip side of the heating medium 34. However, in order to transfer heat generated by the heater 35a to the heating medium 34, a joining method that does not impede heat transfer from the core 35b to the heating medium 34 is preferably employed.

The holder 35c is joined to the tip of the core 35b and holds the heater 35a at a predetermined position. In order to exhibit this function, the holder 35c has a greater diameter than that of the heater 35a.

The insulation sheath 35d covers the periphery of the heater 35a and thus functions as an insulation layer for preventing the heat generated by the heater 35a from directly affecting the inner surface of the container 100. In order to further exhibit the function as the insulation layer, the insulation sheath 35d is preferably disposed at a distance from the heater 35a so that the inner peripheral surface thereof does not come into contact with the heater 35a.

The insulation sheath 35d may be made of the same metal material as that of the tube body 32 or a ceramic material. However, when the function as the insulation layer is emphasized, it is advantageous that a ceramic material having a lower thermal conductivity than that of the metal material is used.

The heat source 35 described above is disposed on the opposite side of the tube body 32 with respect to the heating medium 34 in the axial direction of the tube body 32. In addition, the dimensions in the radial direction of the heat source 35 are equal to or smaller than those of the tube body 32. Therefore, the heat source 35 can be prevented from becoming an obstacle to insertion and removal of the sterilant supply tube 31 into and from the container 100.

Next, the container holding unit 50 is configured as a device called, for example, a gripper that holds the container 100. As the gripper, a well-known device which grips and holds a neck 101 of the container 100 may be used. The grippers are provided at equal intervals on the outer periphery of the transporting star wheels 17 to transport the containers to predetermined positions while gripping the containers 100 transported during the previous processes.

Hereinafter, a procedure of sterilizing the inside of the container 100 using the sterilization device 11 will be described.

When the container 100 is transported to the sterilization position, the elevating bar 36 located at the standby position illustrated in FIG. 3 is lowered to the operation position illustrated in FIG. 2 such that the sterilant supply tube 31 is inserted into the container 100 and the sterilization process is started. At this time, power is supplied from the power source to the heater 35a to heat the heating medium 34 to a temperature higher than the boiling point of the sterilant. For example, in a case where peracetic acid is used as the sterilant, since the boiling point of the peracetic acid is near 107° C., the heating medium 34 is heated to a temperature higher than 107° C., for example, 120° C. to 200° C.

Next, by operating the syringe pump of the sterilant supply unit 11a, the sterilant is discharged from the discharge port 33a of the needle 33 toward the heating medium 34 such that the sterilant D in droplet form is dropped in a downward direction A as illustrated in FIG. 4(b). The amount of discharged sterilant is arbitrary. However, according to examination performed by the inventors, it was confirmed that a 500 ml (milliliters) PET bottle can be sufficiently sterilized by using only about 0.2 ml of an aqueous solution of peracetic acid having a concentration of 10%.

The sterilant that reaches the heating medium 34 immediately becomes vapor as illustrated in FIG. 4(*c*) because the heating medium 34 is heated to a temperature higher than the boiling point of the sterilant. The sterilant that becomes the vapor S moves upward toward the rear end of the sterilant supply tube 31 from the heating medium 34. However, since the ventilation passages 32*a* are formed in the sterilant supply tube 31, the sterilant that becomes vapor sequentially passes through a sterilant passage 32*b* which is the inside of the tube body 32 and the ventilation passages 32*a* and leaks out of the sterilant supply tube 31. The sterilant that passes through the ventilation passages 32*a* then adheres to the inner surface of the container 100 and sterilizes the inner surface thereof.

Sterilization performed in the above-described manner is performed on each of the containers 100.

Next, the actions and effects of the sterilant supply unit 30 of the sterilization device 11 will be described.

Since the sterilant supply unit 30 performs sterilization by vaporizing the sterilant in the container 100, necessary members starting from the sterilant supply tube 31 may have small sizes and may also be reduced in number. Therefore, the cost of the sterilization device 11 can be reduced. Moreover, each of the sterilant supply units 30 can perform sterilization by vaporizing the sterilant having a high concentration in the container 100 and thus can obtain high sterilizing ability.

In addition, since the periphery of the heater 35*a* is covered with the insulation sheath 35*d*, an effect caused by heating which is necessary to vaporize the sterilant by using the sterilant supply unit 30 can be limited to the temperature limit of the container 100, for example, a temperature of lower than 70° C. to 80° C. in case of the PET bottle.

In addition, in the sterilant supply unit 30, since the ventilation passages 32*a* are provided at a plurality of points in the axial direction and the peripheral direction of the tube body 32, the sterilant vaporized by the heating medium 34 easily passes through the tube body 32 and can adhere to the inner surface of the container 100. Therefore, the sterilization device 11 can obtain high sterilizing ability.

In addition, in the sterilant supply unit 30, the discharge port 33*a* of the needle 33 is positioned closer to the tip side than the rearmost ventilation passage 32*a*. Therefore, the needle 33 acts as resistance against the second and first ventilation passages 32*a* from the rearmost side, and thus it can be said that the sterilant that moves upward between the ventilation passages 32*a* and the needle 33 easily passes through the ventilation passages 32*a*.

Furthermore, in the sterilant supply unit 30, in a case where a plurality of droplets of the sterilant are continuously dropped into a single container 100, the vaporization rate of the subsequent sterilant can be increased. That is, while the previously dropped sterilant is vaporized and moves upward, when the subsequent sterilant is dropped, the subsequent sterilant is heated in the process of passing through the vaporized sterilant and then reaches the heating medium 34. Therefore, the vaporization rate of the sterilant is increased, and thus an increase in the efficiency of the sterilization process can be achieved.

In the invention, the configurations employed by the first embodiment can be selected or can be appropriately changed to other configurations.

Figure 5:
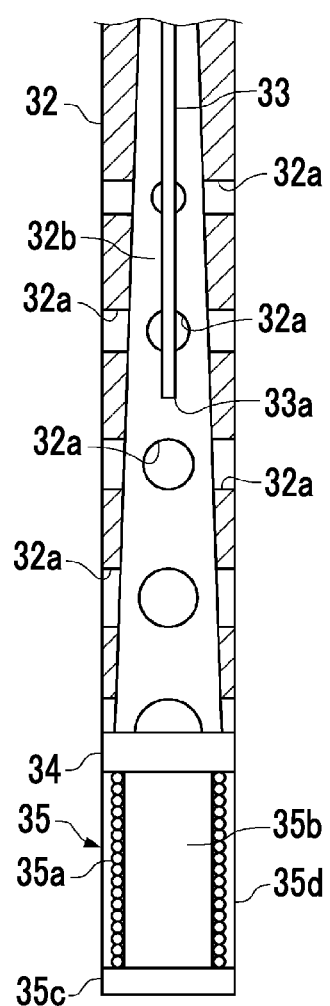
FIG. 5 is a view illustrating a modification example of the sterilant supply tube in the first embodiment.

For example, the inner diameter of the tube body 32 is uniform in the axial direction. However, the invention is not limited thereto. For example, as illustrated in FIG. 5, the inner diameter thereof may be reduced toward the rear end. In this case, a pressure loss in the vaporized sterilant is increased toward the rear end of the tube body 32, and thus the sterilant can easily pass through the ventilation passages 32*a*. In addition, in the example of FIG. 5, the diameters of the ventilation passages 32*a* aligned in the axial direction are reduced toward the rear end, and thus the sterilant can easily pass through the ventilation passages 32*a* on the tip side.

Figure 6:
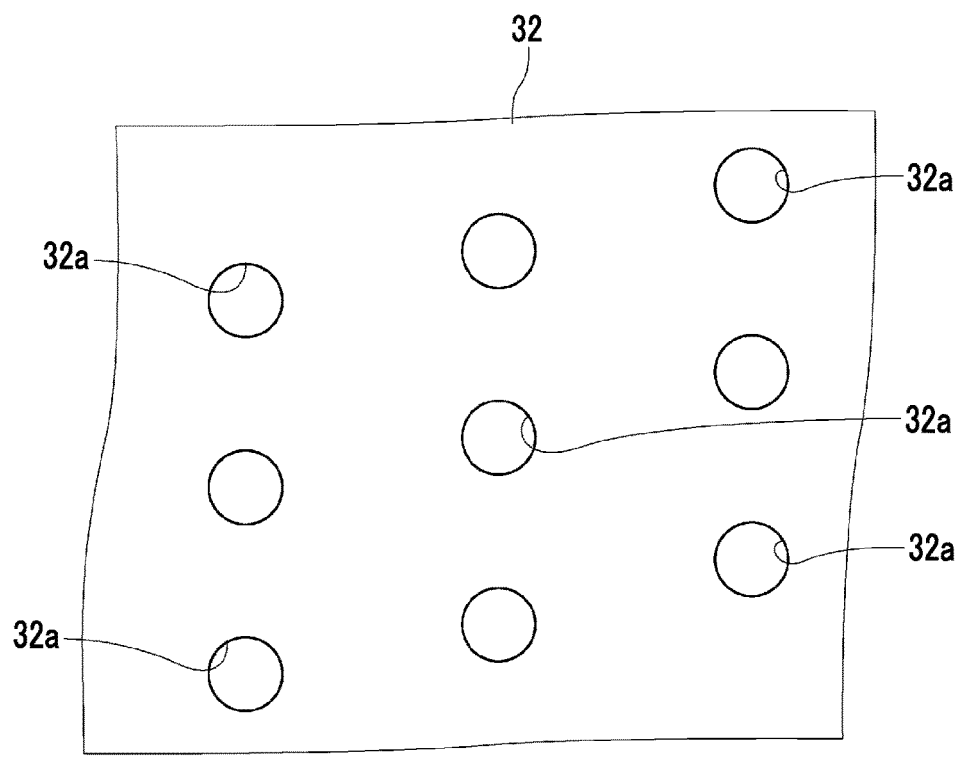
FIG. 6 is a view illustrating a modification example regarding the arrangement of ventilation passages in the first embodiment.

In addition, in the first embodiment, the ventilation passages 32*a* are aligned in the axial direction and are aligned in the peripheral direction. However, the invention is not limited thereto. For example, when the tube body 32 is deployed, as illustrated in FIG. 6, the ventilation passages 32*a* may also be arranged in a zigzag lattice pattern. It is assumed that the sterilant easily leaks out of the tube body 32.

Second Embodiment

Next, a second embodiment of the invention will be described with reference to FIGS. 7 to 8(*c*). The second embodiment is similar to the first embodiment in that the sterilant is vaporized in the container 100 and is different therefrom in means for vaporizing the sterilant. Hereinafter, the second embodiment will be described focusing on the differences therebetween.

In the second embodiment, when sterilization is performed, a sterilant supply tube 41 of a sterilant supply unit 40 is inserted into the inverted container 100 from below. When sterilization is ended, the sterilant supply tube 41 is lowered and removed from the container 100.

Figure 7:
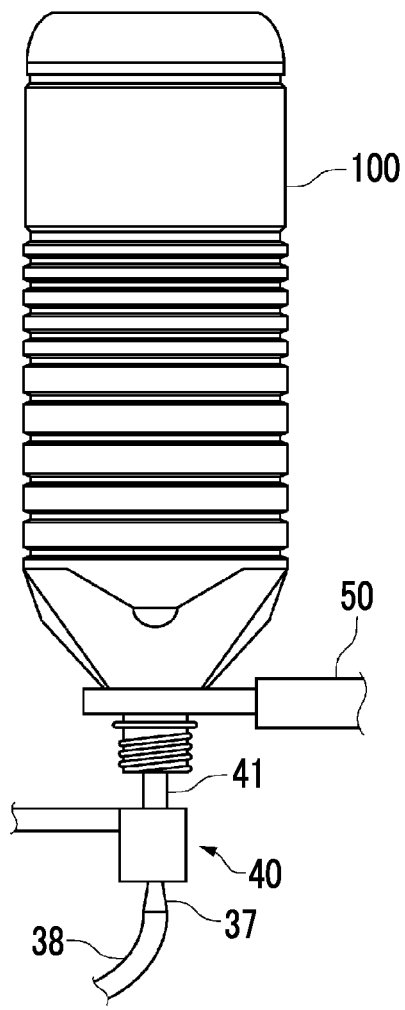
FIG. 7 is a view illustrating a sterilization device for a container in a second embodiment of the invention.

As illustrated in FIGS. 7 to 8(*c*), the sterilant supply tube 41 includes a hollow cylindrical tube body 42, a needle 43 which is disposed inside the tube body 42 to discharge the sterilant toward a heating medium 44, and a nozzle 37 which supplies the sterilant to the needle 43. In addition, even in the second embodiment, a side on which the sterilant supply tube 41 is inserted into the container 100 is defined as the tip, and the opposite side thereof is defined as a rear end.

The tube body 42 is made of the same material as that of the tube body 32 of the first embodiment and is formed of a member which does not include the ventilation passages 32*a* and has a simple tube shape in which both ends in the axial direction are open.

In addition, the needle 43 has the same configuration as that of the needle 33 of the first embodiment except for the disposition. That is, a discharge port 43*a* of the needle 43 is disposed to be surrounded by the heating medium 44, and the sterilant D in droplet form discharged from the discharge port 43*a* passes through the inside of the heating medium 44 while moving upward inside the tube body 42.

The heating medium 44 heats and vaporizes the sterilant that moves upward.

The heating medium 44 is formed of electric heating wires wound in a spiral ring form and mounted on the inside of the tube body 42 and surrounds a sterilant passage 42*b* inside the tube body 42 from the entire region thereof in the peripheral direction. The heating medium 44 is fixed to the inner peripheral surface of the tube body 42 and is thus held in the tube body 42. A ceramic tube which acts as an insulation material may also be interposed between the heating medium 44 and the tube body 42.

When power is supplied from a power source (not illustrated) to the heating medium 44, the heating medium 44 generates heat. The electric heating wires used in the heating medium 44 are the same as those of the first embodiment.

Hereinafter, a procedure of sterilizing the inside of the container 100 using the sterilant supply unit 40 will be described.

When the container 100 is transported to the sterilization position, as illustrated in FIGS. 7 to 8(c), the sterilant supply tube 41 is inserted into the container 100 and the sterilization process is started. At this time, power is supplied from the power source to the heating medium 44 and thus the heating medium 44 is heated to a temperature higher than the boiling point of the sterilant. The heating temperature is the same as in the first embodiment.

Next, by operating a syringe pump, as illustrated in FIG. 8(b), the sterilant D in droplet form is discharged from the discharge port 43a of the needle 43 in an upward direction A toward the heating medium 44. The amount of discharged sterilant may be the same as that of the first embodiment, and the sterilant is discharged at a speed such that the sterilant can reach the sterilant passage 44a of the heating medium 44.

Since the heating medium 44 is heated to a temperature higher than the boiling point of the sterilant, as illustrated in FIG. 8(c), the sterilant that passes through a region surrounded by the heating medium 44 becomes vapor S in the process of moving upward though the sterilant passage 42b. The sterilant that becomes the vapor S leaks out from an opening (ventilation passage) at the rear end of the sterilant supply tube 41 positioned on the downstream side in a direction in which the sterilant is discharged, flows into the container 100, adheres to the inner surface of the container 100, and sterilizes the inner surface.

Sterilization performed through the above-described procedure is performed on each of the containers 100.

The actions and effects of the sterilant supply unit 40 will be described.

Similar to the sterilant supply unit 30, the sterilant supply unit 40 can also obtain high sterilizing ability at low cost.

In addition, in the sterilant supply unit 40, since the periphery of the heating medium 44 is covered with the tube body 42, an effect of heating needed to vaporize the sterilant can be suppressed to a temperature of lower than the temperature limit of the container 100.

In the sterilant supply unit 40, the ability of the heating medium 44 to heat the sterilant can be adjusted by changing the length thereof in the axial direction or dividing the electric heating wires in the axial direction. Therefore, even when the amount of supplied sterilant is changed, by adjusting the heating ability as necessary, the sterilant can be vaporized without omissions.

In addition, since the sterilant is discharged in the upward direction, even when the sterilant is discharged from the discharge port 43a of the needle 43 while not being vaporized, the sterilant falls thereafter. Therefore, a risk that the sterilant may adhere to the inner surface of the container 100 as droplets and remain in the beverage therein can be reduced.

While the invention has been described above on the basis of the first and second embodiments, the configurations employed by the embodiments can be selected or can be appropriately changed to other configurations without departing from the spirit of the invention.

For example, the configuration of the aseptic beverage filling machine 1 is merely an example, and the sterilization device of the invention can be applied to another type of aseptic beverage filling machine.

In addition, the first embodiment can also be applied to the sterilization of an inverted container, or the second embodiment can also be applied to the sterilization of an upright container.

REFERENCE SIGNS LIST 1 aseptic beverage filling machine
10 importing conveyor
11 sterilization device
11a sterilant supply unit
13 rinsing device
14 filling device
15 capper
16 exporting conveyor
17 transporting star wheel
20 cap
21 base support
30, 40 sterilant supply unit
31, 41 sterilant supply tube
32, 42 tube body
32a ventilation passage
32b, 42b sterilant passage
33, 43 needle
33a, 43a discharge port
34, 44 heating medium
35 heat source
35a heater
35b core
35c holder
35d insulation sheath
36 elevating bar
37 nozzle
38 tube
39 guide rail
50 container holding unit
100 container
C chamber

The invention claimed is:

1. A sterilization device comprising:
   a sterilant supply tube which has a sterilant passage inside the sterilant supply tube, through which a discharged sterilant in liquid form passes in a state in which the sterilant supply tube is inserted into a container as a sterilization object;
   a heating medium which heats and vaporizes the sterilant that passes through the sterilant passage;
   a ventilation passage which allows the sterilant heated and vaporized by the heating medium to leak out of the sterilant supply tube; and
   an elevator which moves the sterilant supply tube between an operation position located inside the container and a standby position located outside the container,
   wherein the heating medium is disposed to block a downstream end of the sterilant passage, the downstream end being in a downstream side of the sterilant passage in which the sterilant in the liquid form is discharged.

2. The sterilization device according to claim 1, wherein the ventilation passage is formed in a side surface of the sterilant supply tube and is formed closer to an upstream side in a direction in which the sterilant in the liquid form is discharged than the heating medium, and
   the sterilant that reaches the heating medium and vaporizes leaks out through the ventilation passage formed in the side surface of the sterilant supply tube.

3. The sterilization device according to claim 2, wherein the ventilation passage includes a plurality of ventilation passages formed in the side surface of the sterilant supply tube.

4. The sterilization device according to claim 2, wherein a heat source which heats the heating medium is disposed on an opposite side of the sterilant supply tube with respect to the heating medium in an axial direction of the sterilant supply tube and has dimensions in a radial direction that are equal to or smaller than those in a radial direction of the sterilant supply tube.

5. The sterilization device according to claim 3, wherein a heat source which heats the heating medium is disposed on an opposite side of the sterilant supply tube with respect to the heating medium in an axial direction of the sterilant supply tube and has dimensions in a radial direction that are equal to or smaller than those in a radial direction of the sterilant supply tube.

6. The sterilization device according to claim 3, wherein a discharge port from which the sterilant in liquid form is discharged is positioned in the downstream side from one of the plurality of ventilation passages positioned in a upstream side in the direction in which the sterilant in the liquid form is discharged.

7. The sterilization device according to claim 3, wherein the plurality of ventilation passages is arranged at the upstream side in the direction in which the sterilant in the liquid form is discharged with respect to the heating medium.

8. The sterilization device according to claim 1, wherein the sterilant supply tube comprises a tube body defining the sterilant passage, and the heating medium is configured to seal a tip of the tube body.

9. The sterilization device according to claim 1, wherein the sterilant supply tube comprises a heat source which heats the heating medium, the heat source having an insulation layer.

10. The sterilization device according to claim 1, wherein the sterilant supply tube includes a heat source arranged under the heating medium to heat the heating medium, and an insulation layer surrounding around the heat source to prevent heat of the heating source from directly affecting the container as the sterilization object.

* * * * *